United States Patent [19]

Galante et al.

[11] Patent Number: 5,187,368

[45] Date of Patent: Feb. 16, 1993

[54] DETECTION METHOD FOR LIQUIDS USING NEAR INFRARED SPECTRA

[75] Inventors: Leonard J. Galante, Cary, N.C.; Robert A. Lodder, Lexington, Ky.

[73] Assignees: Glaxo Inc.; The University of Kentucky, RTP, N.C.

[21] Appl. No.: 581,823

[22] Filed: Sep. 12, 1990

Related U.S. Application Data

[63] Continuation-in-part of Ser. No. 414,799, Sep. 29, 1989, abandoned.

[51] Int. Cl.[5] .................. G01N 21/35; G01N 21/51
[52] U.S. Cl. .................... 250/341; 250/339; 250/343; 250/358.1; 356/341; 356/407
[58] Field of Search .............. 250/341, 339, 574, 343, 250/358.1, 359.1; 356/338, 51, 407, 337, 341

[56] References Cited

U.S. PATENT DOCUMENTS

| | | |
|---|---|---|
| 4,118,625 | 10/1978 | Underwood ................. 250/343 |
| 4,367,041 | 1/1983 | Webb, Jr. et al. .............. 356/72 |
| 4,755,048 | 7/1988 | Kaufman ...................... 356/407 |
| 4,768,879 | 9/1988 | McLauchlan et al. .......... 356/335 |
| 4,969,741 | 11/1990 | Kennedy et al. ............... 356/338 |
| 4,998,824 | 3/1991 | Littlejohn et al. .............. 356/407 |

FOREIGN PATENT DOCUMENTS 8909931 10/1989 PCT Int'l Appl. ............ 356/240

Primary Examiner—Carolyn E. Fields
Attorney, Agent, or Firm—David J. Levy; Charles T. Joyner

[57] ABSTRACT

A method for detecting the presence or absence of microorganisms in a liquid test sample is provided without need for withdrawing an aliquot or destroying the sample. The method comprises taking near-infrared spectra of the sample and comparing it visually or mathematically to the spectra of a standard, which may be the values of the spectra known to the operator or may be a standard sample that is provided and run side-by-side.

14 Claims, 11 Drawing Sheets

GROWTH PATTERN FOR ASPER. NIGER

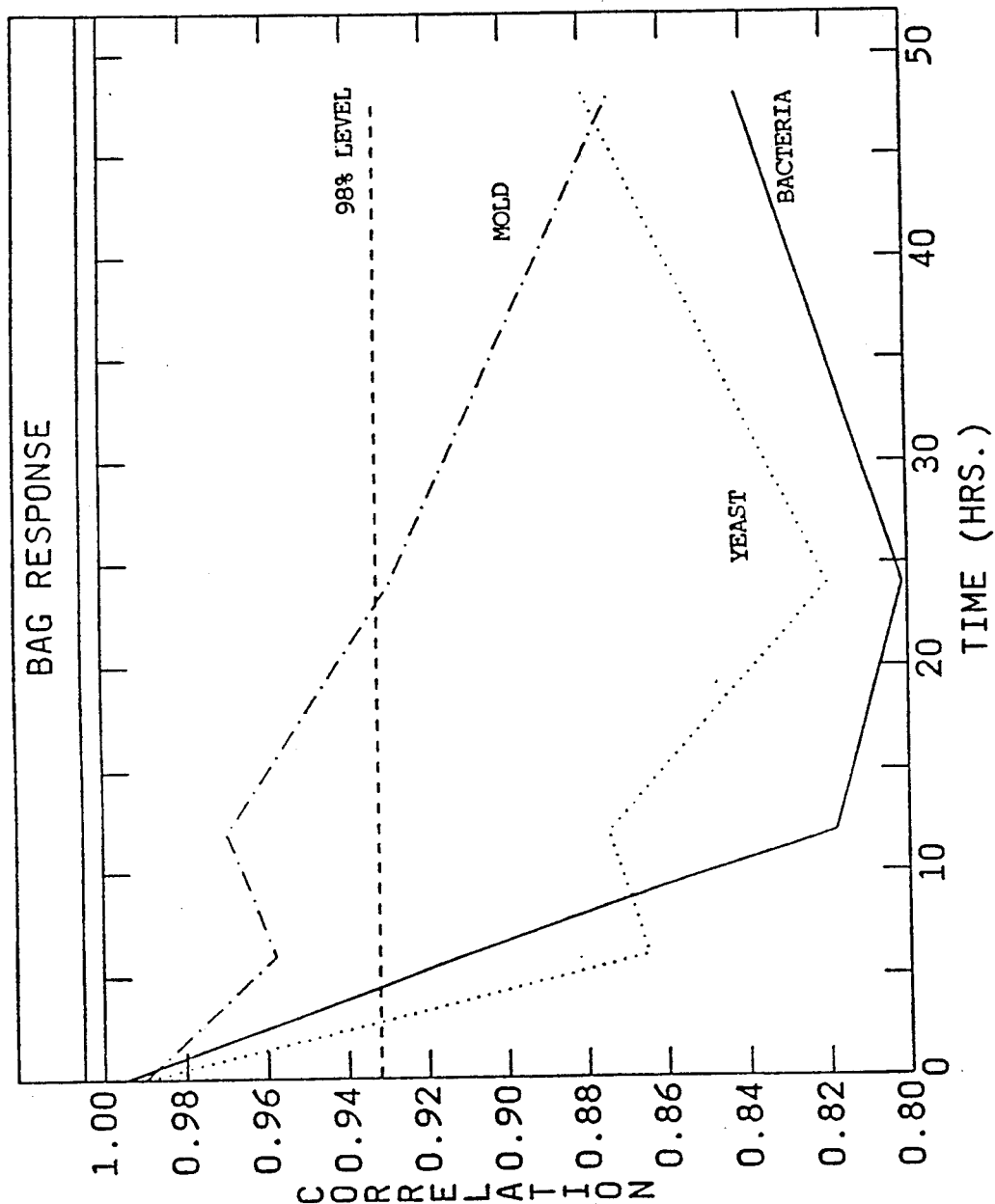

DETECTION METHOD FOR LIQUIDS USING NEAR INFRARED SPECTRA

This Application is a continuation-in-part of U.S Ser. No. 07/414,799 filed Sept. 29, 1989, now abandoned.

BACKGROUND OF THE INVENTION

Biotechnology has created a number of new and potentially life-saving products Many of these products cannot withstand exposure to the digestive tract as an oral formulation and must instead be formulated as injectables. Furthermore, these molecules may not survive terminal sterilization by autoclaving. In these cases, an aseptic-filling process is required although it is a less reliable sterilization method, making detection of unsterile products a necessary task. Conventional microbiological methods and turbidimetry are currently employed as inspection techniques to assess sterility. However, these procedures are typically very time consuming, invasive, and may not detect low levels of contamination.

In more detail, many drugs must be formulated as parenteral products (injectables), and delivered in a solution contained in a sterile vial or intravenous (IV) bag. Maintaining the stability of the drug (preventing decomposition) and insuring the sterility of the drug (absence of microbial growth) can be a problem.

Preservative systems and sterilization procedures for parenteral products must be well monitored (see Henry L. Avallone, *J. Parenter. Sci. Technol.* 1985, 39(2), 75-79) and tested by validated microbiological methods (see "Validation of Steam Sterilization Cycles", Technical Monograph No. 1, and "Validation of Aseptic Filling For Solution Drug Products", Technical Monograph No. 2, Parenteral Drug Association, Inc., 1980). The typical method of assuring the sterility of vials and IV bags is to fill them with the desired product and sterilize the final filled product by autoclaving (see John Y. Lee, *Pharmaceutical Technology* 1989, 13(2), 66-72). Unfortunately, the autoclaving process can also stress fragile molecules and denature proteins. In such cases, the IV bag or vials are filled aseptically (under conditions that are as sterile as possible) and sterilized by filtration with a 0.2 $\mu$m filter. The product can then be used.

Unfortunately, sterility by aseptic filling is not as certain as with terminal sterilization (autoclaving). It has been estimated that terminal sterilization by autoclaving results in a sterility assurance level of $10^{-6}$ or better (probability of an unsterile unit), while aseptic filling generally achieves an assurance level of only $10^{-3}$ or one contaminated unit per thousand (see *Quality Control Reports: The Gold Sheet*, in F-D-C Reports, Bill Paulson, Ed., 1988, 22(3), 1-6 and Henry L. Avallone, *J. Parenter. Sci. Technol.* 1986, 40(2), 56-57). Because of this difference in sterility assurance levels FDA is requiring manufacturers who produce aseptically-filled products to submit methods and data justifying why terminal sterilization cannot be used. The manufacturer must also describe the microbiological monitoring and control procedures used to assure sterility (see FDA Guideline on Sterile Drug Products Produced by Aseptic Processing; Food and Drug Administration, Rockville, Md., July, 1987).

The challenge to the analyst is to determine which product is contaminated and to prevent its use, assuring that the final occurrence of defective units is very low. Perhaps the simplest method of assuring product sterility involves the incubation of an IV bag or vial until any microorganisms that might be present grow sufficiently numerous that turbidity develops. The turbidity is then detected by ordinary optical methods or by visual examination. Also, microscopic examination would reveal the identity of the contaminating microorganism(s). Unfortunately, it can take a significant amount of time for turbidity to develop, and products contaminated with small amounts of microorganisms such as bacteria, molds, or yeast might not show visible turbidity. Furthermore, some IV bags or vials are composed of materials that interfere with the visible detection of turbidity.

U.S. Pat. No. 4,367,041 to Webb teaches a liquid chromatography method where pure components of a mixture may be separated during chromatography by measurement of the ratio of absorbance at two wavelengths.

A system for detecting the tampering of capsules using near-infrared (near-IR) light is described by Robert A. Lodder et al. in *Anal. Chem.* 1987, 59, 1921-1930. Near-IR methods are commonly applied to the analysis of aqueous samples, see Robert A. Lodder et al., *Appl. Spectrosc.* 1988, 42, 518-519 and have been used in the detection of contaminated products, see Robert A. Lodder et al., *Appl. Spectrosc.* 1988, 42(8), 1351-1357 and 1500-1512, and *Appl. Spectrosc.* 1988, 42(4), 556-558.

An analytical method that would enable the detection of low levels of microorganisms in parenteral products without the need for incubation for a long period of time would represent a significant advance in the analysis of parenteral products. Such a method would preferably be used to detect contamination by bacteria, yeast, or molds in drug vials and IV bags.

SUMMARY OF THE INVENTION

The present invention comprises an analytical method based on the near-IR light intensity change, e.g., light scattering or absorption, as a method for detecting small quantities of microorganisms in drug products e g., in sealed bags or vials. The method is noninvasive and nondestructive, preventing possible contamination of bag or vial units by the analytical method itself Ordinarily, sterility testing and microbial identifications are accomplished by looking at only a small number of units from the total lot of a product because these microbiological tests are, time consuming, laborious, invasive, and in essence destroy the product that is being examined.

Near-IR light back-scattering is used as a method for determining low levels of contamination noninvasively and nondestructively. The method is used to detect contamination by yeast, mold, and/or bacteria with a detection limit potentially as low as three cfu of yeast per mL. Using the near-IR method of the invention, each container, e.g. IV bag or vial, can be evaluated intact with its sterility maintained, allowing the product to be used or evaluated by another method.

BRIEF DESCRIPTION OF THE DRAWINGS

FIG. 11 depicts the change in correlation of test bags as mold, yeast and bacteria grow in the bag compared to their respective values immediately after inoculation.

DETAILED DESCRIPTION OF THE INVENTION

Figure 1:
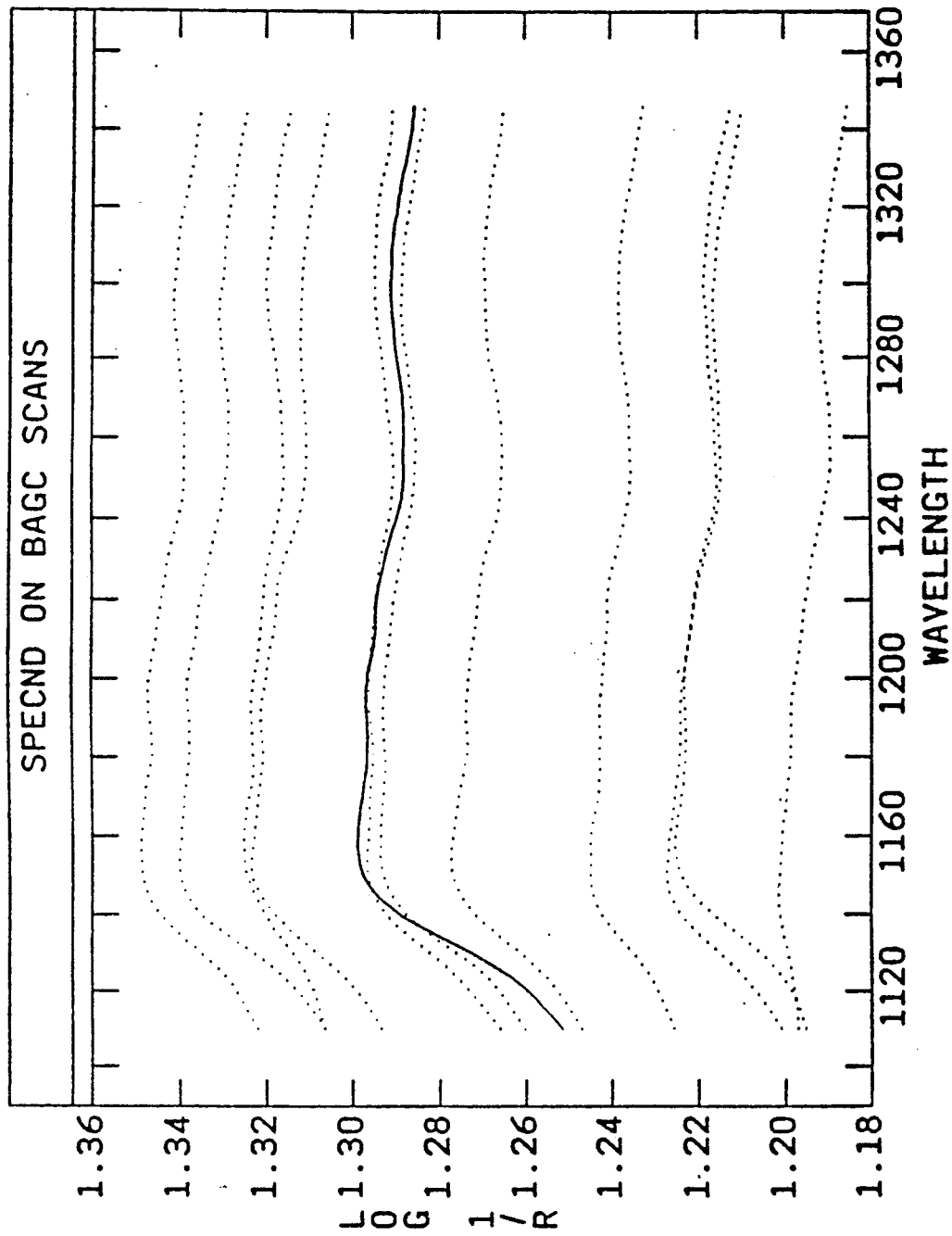
FIG. 1 depicts 11 traces of the near infrared spectra of a PVC IV bag containing 5% dextrose injection USP and 0.5 mg per mL of ranitidine as the hydrochloride. The "log l/R" indicates the logarithm of the reciprocal of the reflectance intensity of the radiation.

As used in the present specification, a near-IR spectrum is a spectrum of the scattering (or reflectance) of light introduced into a liquid sample. This is a physical phenomenon and is, in effect, a deflecting of the incident near-IR light. Such is not an absorbance or transmittance spectrum as in the more typical IR spectra which are indicative of the individual chemical structural features, of a chemical compound. Since the scattering method of the invention depends on the amount of scattered (or reflected) light, any absorbance in the liquid sample will decrease the quantity of light available for scattering.

The present invention comprises a method for the detection of microorganisms in a liquid sample to be tested, which comprises the step of obtaining a near-IR spectrum of the liquid sample and then comparing the spectrum to a standard sample. In more detail, the detection of microorganisms will often be for the purpose of determining sterility (or the lack of sterility) in the liquid sample. Examples of microorganisms include any living cells which are individually not detected by visual inspection. Specific examples include yeast, bacteria or mold. The liquid sample to be tested is, in particular, water or an aqueous IV solution such as a solution of dextrose, typically 5% (w/v), or isotonic sodium chloride solution e.g., about 0.9% w/v. Other liquid samples that can be evaluated according to the method of the present invention include aqueous solutions used as growth media for fermentation stock or the growth of other cells. In this case, one would detect the presence and quantity of cells in order to determine whether or not there is sufficient population of the cells for the purpose intended. In contrast, if the method of the present invention were used to determine sterility, the object of the exercise would be to confirm whether or not the liquid sample is sterile as seen by the absence of microorganisms.

Typical microorganisms to be detected according to the method of the present invention include yeast, bacteria and mold. Other cells include algae and other living cell lines such as cancer cell lines.

The infrared spectrum to be taken according to the method of the present invention is a spectrum in the range of about 800–2500 nanometers (nm), more particularly 1100–1360 nm. The spectrum can be taken on any conventional near-IR spectrophotometer such as the InfraAlyzer 500 from Bran+Luebbe of Elmsford, N.Y., the 6500 spectrophotometer from NIR Systems of Silver Springs, Md. and the Quantum 1200 spectrophotometer from LT Industries of Silver Springs, Md. In particular, the InfraAlyzer 500 can be used according to the method of the present invention because it is a double beam instrument and therefore need not be corrected for variations such as fluctuations in source intensity.

The near-IR spectrophotometer utilized is configured to detect scattering of the incident beam or changes in back-reflected light intensities because of absorption processes. Detection of scattered or back-reflected light from the incident beam can be accomplished by installing equipment for light scattering as known in the art. For example, the EDAPT-1 probe, available from Bran+Luebbe is suited for this purpose. Adaptation of commercially available near-infrared spectrophotometers for the detection of scattered light is described by Robert A. Lodder et al. in *Appl. Spectrosc.* 1988, 42, 518–519 and in Appl. Spectrosc. 1988, 42(4), 556–558. Other methods for detecting light scattering to be used in the method of the present invention are those described in the chapter entitled "Molecular Scattering Methods" in *Spectrochemical Analysis* by James D. Ingle and Stanley R. Crouch, pp. 494–524, Prentice Hall, Englewood Cliffs, N.J., 1988.

The liquid sample to be tested according to the invention is, in particular, held in a container which is at least partially transparent to at least one wavelength of near-infrared light. As the spectrophotometer scans the near-infrared sp®ctrum at those wavelengths wherein both the liquid medium and the container holding the medium are at least partially transparent, the spectrophotometer will then detect changes in the light that passes through the container and medium and is reflected back or scattered due to the presence of the microorganisms to be detected. Examples of the container include bags, bottles, tubes, vials and ampules of glass (e.g., high grade borosilicate glass) or an organic polymer (e.g., PVC, polyethylene and CR3 polymer from Abbott Laboratories, Chicago, Ill.). In particular, the method of the invention can be used to detect the sterility or loss of sterility, being more precise, of a liquid for parenteral administration to humans. Examples of parenteral administration include IV and intramuscular injections or irrigation of a wound or other body cavity. The liquid medium may be composed of only a fluid for administration or it may contain a pharmaceutical formulation such as ranitidine hydrochloride injection. In addition to checking the sterility of an aseptically refilled container, wherein a concern is the growth of microorganisms, the method of the present invention can also be used, conversely, to check the presence of such microorganisms that are beneficial e.g., wherein one would want to check that the growth of bacteria in a fermentation broth had been proceeding satisfactorily. A particular application of the present invention is the determination of sterility in an aseptically-filled container adapted for administration of its contents to a human.

Once the spectra for the test sample and standard ("training") samples are obtained, the spectra are compared. Comparison may be by visual inspection of the spectra (e.g., in the range of 1100-1360 nm by measuring the log of the reciprocal of reflectance). In general, several e.g., 10 spectra will be taken for each sample at various locations through the container. The trace of each of the spectra of the negative log of reflectance (or the log of the reciprocal of reflectance) are considered With a liquid sample having an absence of microorganisms e.g., a sterile product, the various traces of the spectra taken at different portions of the container will, in general, have the same shape. In contrast, traces of a product with microorganisms present will show different shapes for the spectra when taken through different portions of the container. In fact, the traces will often cross and such crossing is a good indicator of the presence of microbial contaminants An analysis of the distribution quantiles of near-IR spectral data (Robert A. Lodder et al. in *Appl. Spectrosc.* 1988, 42(8), 1512-1520) provides a powerful means of interpreting light-scattering results. The principal advantage of the near-IR light-scattering method is that every single unit of the product can be examined for sterility without invading and destroying the product. Furthermore, the method appears able to differentiate between different types of microorganisms in solution as well as to isolate the location of the organisms inside the container and determine the number of microorganisms present.

The determination of microorganisms according to the invention is based predominantly upon scattering of near-IR light by solid objects inside the container, e.g. sealed IV bag or vial. Monochromatic near-IR light is directed into the sample, and the solid material in the sample scatters light back into an integrating sphere for collection and detection. A fiber-optic diffuse-reflectance probe is used to collect spectral data from a near-IR beam with a wavelength range from 1100-1360 nm. Light is directed into the sample from a fiber-optic bundle that is placed in the integrating sphere, e.g. a one-inch gold sphere directly opposite the sample window (or beam port). A reference fiber-optic bundle is also present to direct near-IR light into the integrating sphere (refer®nce beam). In particular, one may use such a pseudo-double-beam configuration to compensate for noise caused by bending of the fiber and by source intensity variations. Signal values are recorded as a ratio of intensities between the sample and reference beams. The logarithm of the reciprocal of the reflectance intensity recorded by this method is transmitted to a computer such as a MicroVAX II for analysis.

EXAMPLE 1

Equipment. The spectrometer used to generate the near-IR light that was transmitter through the optical fibers was an InfraAlyzer 500 scanning spectrophotometer (Bran+Luebbe, Inc., Elmsford, N.Y.). The data were actually collected on an IBM PS/2 model 50 computer (IBM Corp., Armonk, N.Y.) running IDAS software (Bran+Luebbe). The collected reflectance values were then transferred to a MicroVAX II computer system (Digital Equipment Corp., Maynard, Mass.) and an IBM 3090-300E vector supercomputer. Spectral data were processed in Speakeasy IV Epsilon (Speakeasy Computing Corp., Chicago, IL) programs that were written specifically for this purpose.

Materials. Thirty PVC IV bags containing 5% dextrose Injection USP (Viaflex ® 150-mL containers, Lot# C092445, Baxter Healthcare Corp., Deerfield, Ill.) were injected with 3-mL of Zantac ® Injection 25 mg/mL ranitidine as the hydrochloride, Glaxo Inc., Research Triangle Park, N.C.). Bags were injected through the additive port with a sterile disposable syringe and 21 G×1.5 in. needle (Becton Dickinson, Rutherford, N.J.). The nominal ranitidine concentration in each bag was 0.5 mg/mL.

The microorganisms injected into the bags included: *Candida albicans* (American Type Culture Collection number 10231), *Aspergillus niger* (ATCC no. 16404), and *Pseudomonas aeruginosa* (ATCC no. 9027). These microorganisms were chosen to include a species of yeast, mold, and bacteria, respectively, which are typically tested to meet USP and FDA requirements.

The inoculum was prepared by transferring the respective microorganism from a lyophilized culture onto a solid agar medium and incubating at suitable temperatures for sufficient growth. For *Pseudomonas aeruginosa*, Trypticase Soy Agar was used, and the incubation time was 18-24 hrs. Sabouraud Dextrose Agar was used for *Candida albicans* and *Aspergillus niger* with incubation times of 40-48 hrs and 7 days, respectively. These agars and incubation times are consistent with harvesting procedures for pharmaceutical microbiological assays (see "Preparation of Inoculum", Section <51>, USP XXII, United States Pharmacopeial Covention, 1989).

Cells were harvested into a sterile conical tube with 5% Dextrose Injection USP instead of sterile saline TS to be consistent with the diluent used in the IV bags. Cell concentrations for each species were adjusted to a target range of 10-100 cfu per 0.10 mL (100-1000 cfu/mL) using 5% Dextrose Injection USP. This range was selected to give a starting target concentration of approximately 1 cfu/mL per bag, which represents a reasonable contaminant load for a sterility violation. The number of cfu per mL in the inoculum of each species was determined in quadruplicate by the spread-plate method. The average inoculum concentrations from four plates were 1650 cfu/mL, 100 cfu/mL, and 120 cfu/mL for *Pseudomonas aeruginosa*, *Candida albicans*, and *Aspergillus niger*, respectively.

The additive port of each of the 30 bags was injected with 0.10 mL of inoculum from one of the three microorganisms (10 bags of each type). The bags were inverted several times to distribute the cells throughout the bag.

Data Analysis. A spectral training set was constructed for each group of 10 bags containing a single variety of microorganism. The spectral training set was collected immediately after injection of the microorganisms. Spectra were also obtained from the bags before injection of the microorganisms. These spectra, however, were not used as the training set because the near-IR method appeared to detect the injection of medium and microorganisms, which results in a large disturbance in the spectra. All ten bags containing the same organism were inoculated sequentially prior to the training-set scans. The time lag between the scanning of the first bag and tenth bag was approximately one hour. Furthermore, 12 scans over the wavelength range from 1100-1360 nm were taken from each bag at different portions of the bag. Therefore, each training set consisted of 10 IV bags containing one of three microorganisms in a 5% dextrose solution with drug. Twelve scans were taken from each bag so that each of the three training sets contained 120 spectral scans. During spectral analysis, a spectrum recorded at 130 wavelengths in the 1100-1360 nm region was projected as a single point in a 260-dimensional hyperspace. Thus, each training set was composed of a cluster of 120 points in a 260-dimensional hyperspace. The analytical procedure located the center of the training set from the spectra recorded at time-zero in a 260-dimensional space and integrated outward steadily in all directions in space from the center of this training set to the "edges" of the training-set cluster (the edges are defined typically as being three multidimensional standard deviations away from the center). This integral forms a function that is compared to a second integral, which is determined by integrating from the center of the combined training set and test set of spectra (where the test set is the spectra of the same group of IV bags as the training set although at a later time, such as 6, 12, 24 or 48 hrs after the injection of microorganisms). The 260-dimensional points from these test-set bags scanned at the later times are projected into the same space as the training-set spectra to form an augmented spectral cluster. Integrating from the center of the augmented set out in all directions at a constant rate produces a second integral. A plot of the first integral versus the second integral is used to form a QQ plot.

Figure 4:
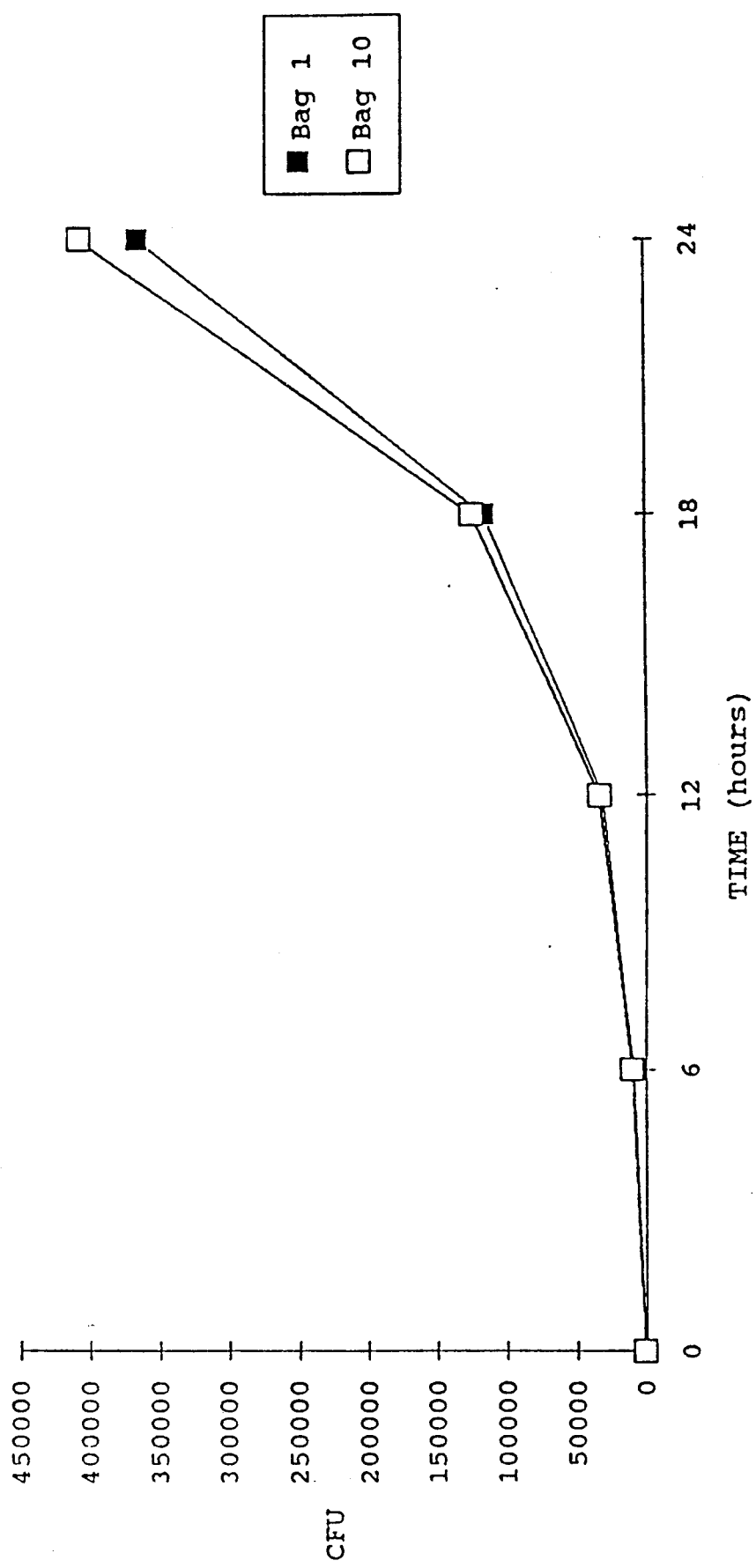
FIGS. 4, 5, and 6 depict the typical growth measured in cfu for a standard bacteria, yeast and mold, respectively, in 150-mL PVC IV bags containing aqueous 5% dextrose and 0.5 mg/mL ranitidine as the hydrochloride.

Microorganism concentrations in bags 1 and 10 from each group were measured at 0, 6, 12, 18, and 24 hrs by removing 0.40 mL of solution from each bag with a 0.5 mL syringe. A 0.10-mL aliquot (or diluted aliquot at high microbiological concentrations) was transferred to each of four plates to determine the average cell concentration in cfu/mL. Trypticase Soy Agar was used as a growth medium for *Pseudomonas aeruginosa* aliquots, colonies were counted after 48 hrs at 30°-35° C. The results of the counts are shown in FIG. 4. Sabouraud Dextrose Agar was used as the growth medium for *Candida albicans* and *Aspergillus niger* aliquots, and colonies were counted after 72 hrs and 7 days, respectively, at 20°-25° C. These data are presented in graphical form in FIGS. 5 and 6.

Calculations. Spectral data are collected at wavelengths $N_{(m)} = (1, 2, \ldots, w)$ on each sample bag. Treatment of collected spectral data I begins with a smoothing process designed to reduce spectral noise:

$$I_{(1)} = W(W(I)) \qquad \text{eq 1}$$

where W represents a linear smoothing operation in which $$i_{ij} = (i_{ij-2} + i_{ij-1} + i_{ij} + i_{ij+1} + i_{ij+2})/5.$$

Calculation of the first derivative of the smoothed spectra removes baseline variations from the spectra of the bag:

$$I_{(d1)i} = \left| \frac{dI_{(1)i}}{dN_{(m)}} \right| \qquad \text{eq 2}$$

A region of interest (i.e., a wavelength region where scattering is expected to be observed from cells) is then selected in the spectra of each bag. The region in this work encompasses one-third of the recorded wavelength spectrum, leading to $s_{(t)} = [w/3]$. A separate set of derivative spectra is then calculated for the region of interest:

$$I_{(d2)i} = \left| \frac{dI_{(1)i\{s_t, s_t+1, s_t+2, \ldots, d\}}}{dN_{(m)\{s_t, s_t+1, s_t+2, \ldots, d\}}} \right| \qquad \text{eq 3}$$

The two spectra from each bag that show the most distinguishing spectral features are selected by:

$$I_{(s1)i} = \sum_{j=1}^{d} i_{(d1)ij} \qquad \text{eq 4}$$

$$I_{(s2)i} = \sum_{j=1}^{d} i_{(d2)ij} \qquad \text{eq 5}$$

$$p_1 = M(I_{(s1)}, \{1, 2, \ldots, u\}) \qquad \text{eq 6}$$
$$p_2 = M(I_{(s2)}, \{1, 2, \ldots, u\}) \qquad \text{eq 7}$$
$$H_{(1)j} = I_{(1)p1j} \qquad \text{eq 8}$$
$$H_{(2)j} = I_{(1)p2j} \qquad \text{eq 9}$$

The distinctive spectra, $H_{(1)}$ and $H_{(2)}$, are combined by:

$$H_{(1)j} = H_{(1)\{w, w-1, w-2, \ldots, 1\}} \qquad \text{eq 10}$$

$$\phi = H_{(1)u} - H_{(2)l} \qquad \text{eq 11}$$

$$H_{(2)j} = H_{(2)j} + \phi \qquad \text{eq 12}$$

$$T_i\{1, 2, \ldots, u\} = H_{(1)j} \qquad \text{eq 13}$$

$$T_i\{u+1, u+2, \ldots, 2u\} = H_{(2)j} \qquad \text{eq 14}$$

$$T_1 = W(T_i) \qquad \text{eq 15}$$

to form an augmented spectral matrix that is useful in quantitative and qualitative analysis. The augmented space T thus has $d = 2u$ dimensions (columns) with one row for each sample bag.

Generally, another m-by-d matrix v, containing validation samples, is also assembled from the same source as the training set is likewise treated in accordance to equations 1-15. The sample set V serves as an indicator of how well the training set describes its overall population variation. New spectra of sample bags under test are denoted X and are also treated in accordance to equations 1-15 before quantitative or qualitative analysis.

Bootstrap distributions are calculated by an operation $\kappa$; and $\kappa(T)$, $\kappa(X)$, and $\kappa(V)$ are each calculated in this manner. The results are the m-by-d arrays B, $B_{(X)}$, and $B_{(V)}$. The operation $\kappa(T)$, for example, begins by filling a matrix P with sample numbers to be used in bootstrap sample sets $B_{(s)}$.

$$P = p_{ij} = r \qquad \text{eq 16}$$

The values in P are scaled to the training-set size by:

$$P = [(n-1)P + 1] \qquad \text{eq 17}$$

A bootstrap sample $B_{(s)}$ is then created for each row i of the m-by-d bootstrap distribution B by:

$$B_{(s)} = t_{Kj} \qquad \text{eq 18}$$

where K are the elements of the i-th rows of P. The q-th row of B is filled by the center of the q-th bootstrap sample, $$b_{qj} = \sum_{i=1}^{n} b_{(s)ij}/n \qquad \text{eq 19}$$

and the center of the bootstrap distribution is:

$$c_j = \sum_{i=1}^{m} b_{ij}/m \qquad \text{eq 20}$$

The operation $\kappa$ is then repeated using X and V.

The multivariate data in the bootstrap distributions are then reduced to a univariate form:

$$s(T)_i = \left( \sum_{j=1}^{d} (b_{ij} - c_j)^2 \right)^{\frac{1}{2}} \qquad \text{eq 21}$$

$$s(X)_i = \left( \sum_{j=1}^{d} (b_{(X)ij} - c_j)^2 \right)^{\frac{1}{2}} \qquad \text{eq 22}$$

$$s(V) = \left( \sum_{j=1}^{d} (b_{(V)ij} - c_j)^2 \right)^{\frac{1}{2}} \qquad \text{eq 23}$$

and these distances are ordered and trimmed according to a trimming-index set:

$$P(T) = \{mp+1, mp+2, mp+3, \ldots, m-mp\} \qquad \text{eq 24}$$

to reduce the leverage effects of isolated selections at the extremes of the bootstrap distributions.

Cumulative Distribution Functions (CDFs) for QQ plotting are formed by:

$$C_{(t)} = \delta(S_{(T)P(T)}, S_{(T)P(T)}) \qquad \text{eq 25}$$

$$C_{(X)} = \delta(S_{(T)P(T)}, S_{(X)P(T)}) \qquad \text{eq 26}$$

$$C_{(V)} = \delta(S_{(T)P(T)}, S_{(V)P(T)}) \qquad \text{eq 27}$$

Graphing either $C_{(X)}$ or $C_{(V)}$ on the ordinate versus $C_{(t)}$ on the abscissa produces a standard QQ plot. Patterns in the QQ plot can be used to analyze structure in the spectral data, and the significance of the correlation between $C_{(t)}$ and $C_{(X)}$ can be used as and indication of the existence of subclusters in the spectral data. In the plot, a straight line with unit slope and an intercept of 0 indicates that the two CDFs are essentially identical (this line should be observed when $C_{(V)}$ is on the ordinate and $C_{(t)}$ is on the abscissa). The presence of breaks in the line indicates that the CDF on the ordinate is multimodal (i.e., that the test set and training set of samples are not the same). Sharp bends in the QQ line also indicate the presence of more than one distribution in the CDF on the ordinate.

The Pearson Product Moment Correlation Coefficient between the two integrals or CDFs is used as a means of quantifying the differences between the test set and training set. The correlation between the two integrals decreases steadily with time when an Iv bag is contaminated. The correlation coefficient can be used to provide both an indication of the number of microorganisms present in a sealed container as well as how long the microorganisms have been present in the container and what kind of microorganisms are present in the container. The identification of microorganisms is accomplished by preparing training sets of each type of microorganism expected in the bag and projecting test spectra into a training set space or library. Overlap should occur between the test group and one of the groups in the training set library if the test bags are contaminated with one of the microorganisms used to develop the training set library.

Microorganism Growth. Each bag contained approximately 0.1 mg/mL phenol because this preservative is present in the drug formulation of Zantac ® Injection. Although this phenol level is insufficient to preserve the bags, it is high enough to decrease organism growth rates. The slightly elevated ambient temperature of the laboratory (30°-35° C.) needed to facilitate operation of the near-IR spectrometer also had an effect on microorganism growth. The high ambient temperature increased the growth rate of *Pseudomonas aeruginosa* but decreased the growth rates of *Aspergillus niger* and *Candida albicans*. These results were determined by storing two duplicate bags for each microorganism at 20°-25° C. and determining their growth-rate profile over 48 hrs in a similar manner. In all cases, solutions remained clear throughout the course of the experiment with no visible signs of product contamination.

Near-IR Results. The baselines and peak heights of repetitive scans differ somewhat because each spectrum was taken at a different location on the Viaflex bag. Accordingly, the thickness of the plastic and aqueous sample sampled can vary somewhat with each scan. Moreover, it is apparent from looking at the near-IR spectra of water and the PVC plastic from the bag that there are only a few relatively narrow spectral regions that may have high sensitivity for looking at back-reflected or scattered light from cells inside vials or bags. The regions around 1450 nm, 1940 nm, and 2500 nm are effectively obscured by intense water absorption. The PVC plastic strongly absorbs around 1720 nm. Therefore, measurements of Near-IR light returning through the water and the bag into the detector in the fiber optic probe should be best in the 1100-1360 nm region, in a small region around 1600 nm, and in the 2000-2400 nm region. Unfortunately, the background absorption in the 2000-2400 nm region from water is still quite high, so this region is virtually useless unless all of the material one wishes to examine is adhered to the bag wall, which minimizes the amount of water that the signal must pass through. The fact that water absorbs more strongly in the "windows" around 1600 nm and 2200 nm than in the window from 1100-1360 nm means that one should be able to determine the location of microorganisms (a type of depth profiling) by looking at spectral absorbances at 1100, 1600, and 2200 nm. For example, light scattering from free-floating microorganisms should appear mainly at the 1100-1360 nm region. However, microorganisms adhering to the walls of the container should appear at the 1600 and 2200 nm regions as well as in the 1100-1360 nm region. In fact, one might expect them to appear more strongly in the 1600 and 2200 nm regions than the 1100-1360 nm region because their absorption coefficients should be higher at the higher near-IR wavel ⑧ngths than at the lower near-IR wavelengths. Therefore, because the pathlength for material adhered to the wall would be very limited, signals for microorganisms adhering to the walls would be expected to be more intense in the 1600 and 2200 nm wavelength regions. Spatial profiling can also be accomplished with the near-IR method. A three-dimensional picture of the contents of the bag can be roughly obtained if the bag is held motionless and multiple scans are obtained by moving the fiber-optic probe.

Figure 7:
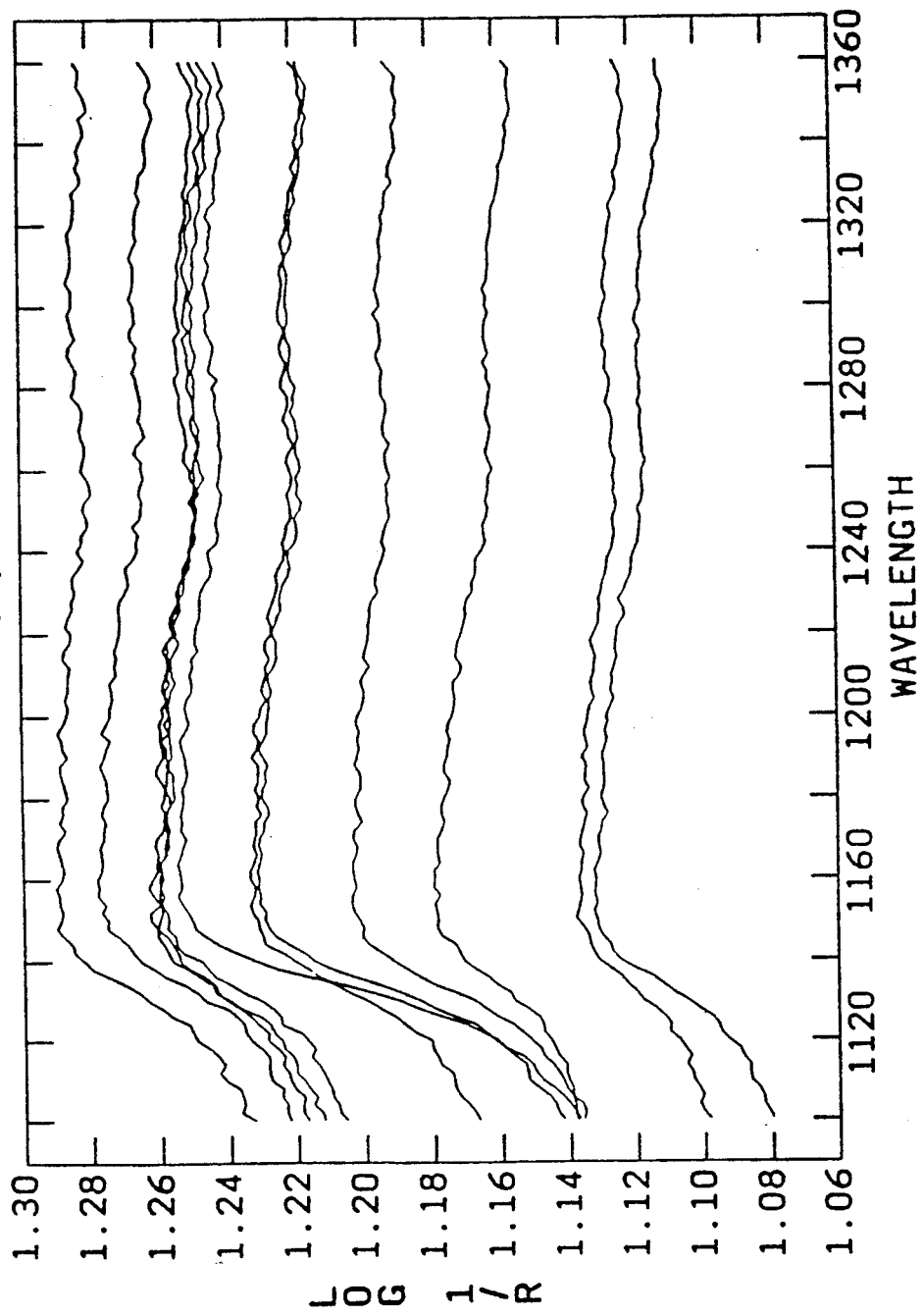
FIGS. 7 and 8 depict the spectra for PVC IV bags containing 5% aqueous dextrose without and with digital filtering, respectively.

In a preliminary study, full spectral scans from 1100-2200 nm were obtained for two inoculated bags. No significant absorbances were observed in the 1600 and 2200 nm regions, and it was believed that microorganisms injected into the bags were floating freely in solution. This study was therefore confined to the 1100-1360 nm region. FIG. 7 shows 12 spectra taken from a single bag. These spectra are raw spectra and are not processed by any filtering methods. They cover the entire spectral range from 1100-1360 nm. The spectra appear to be relatively noisy because very little light is actually reflected back into the probe from the sample. During the first few hrs of cell incubation, few cells are in the solution and very little contamination exists.

Figure 8:
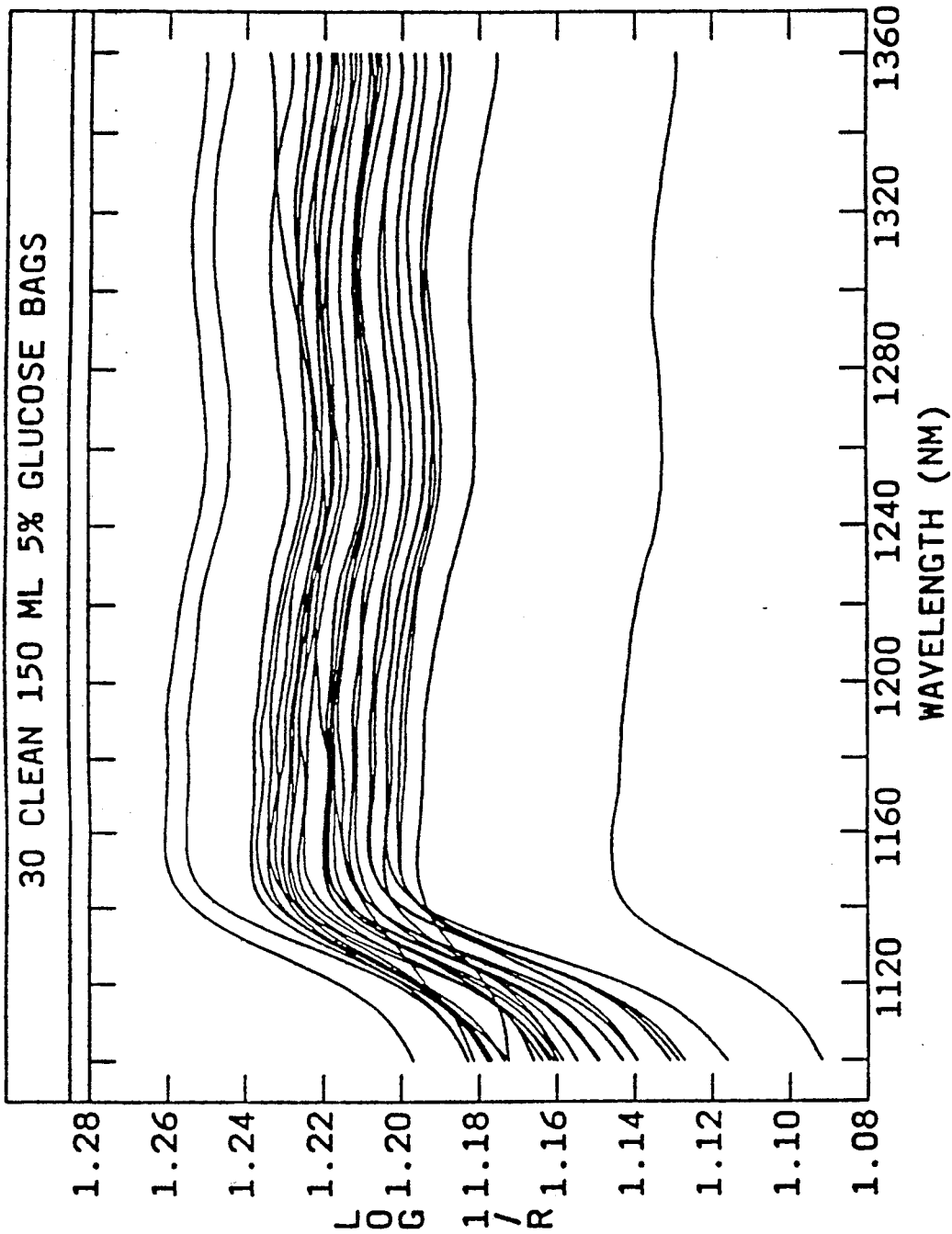

Spectra are filtered digitally and the 12 spectra taken from a single bag are processed to combine them into a single spectrum. The process of digitally filtering the spectra produces smooth and relatively noise-free curves such as those shown in FIG. 8. The data in FIG. 8 come from 30 clean (i.e., uncontaminated), 150 mL, 5% dextrose bags containing drug. At the early stages of contamination, it is important to move the probe around the bag because light will be scattered and reflected back to the probe only in a few locations where cells are present. The observation of scattering during the first few hrs of incubation appears to be somewhat of a statistical phenomenon.

The mathematical problem is first one of identifying which of the 12 spectral scans from a bag actually show back-scattered light. Identifying and quantifying the cells is then accomplished using these particular scans. The first derivative is calculated for each of the 12 spectra and the absolute value of the first derivative in the regions near 1100 nm and 1260 nm were examined more closely. The sum of the absolute values of the first derivatives in these two regions was calculated for each of the 12 spectra, and the spectra showing the maximum sum were used to create a new spectrum. If the same spectrum has the maximum absolute value of the first derivative at both wavelengths, then it is the only spectrum selected, and the resulting, normalized curve is symmetrical around the zero wavelength displacement point.

Figure 2:
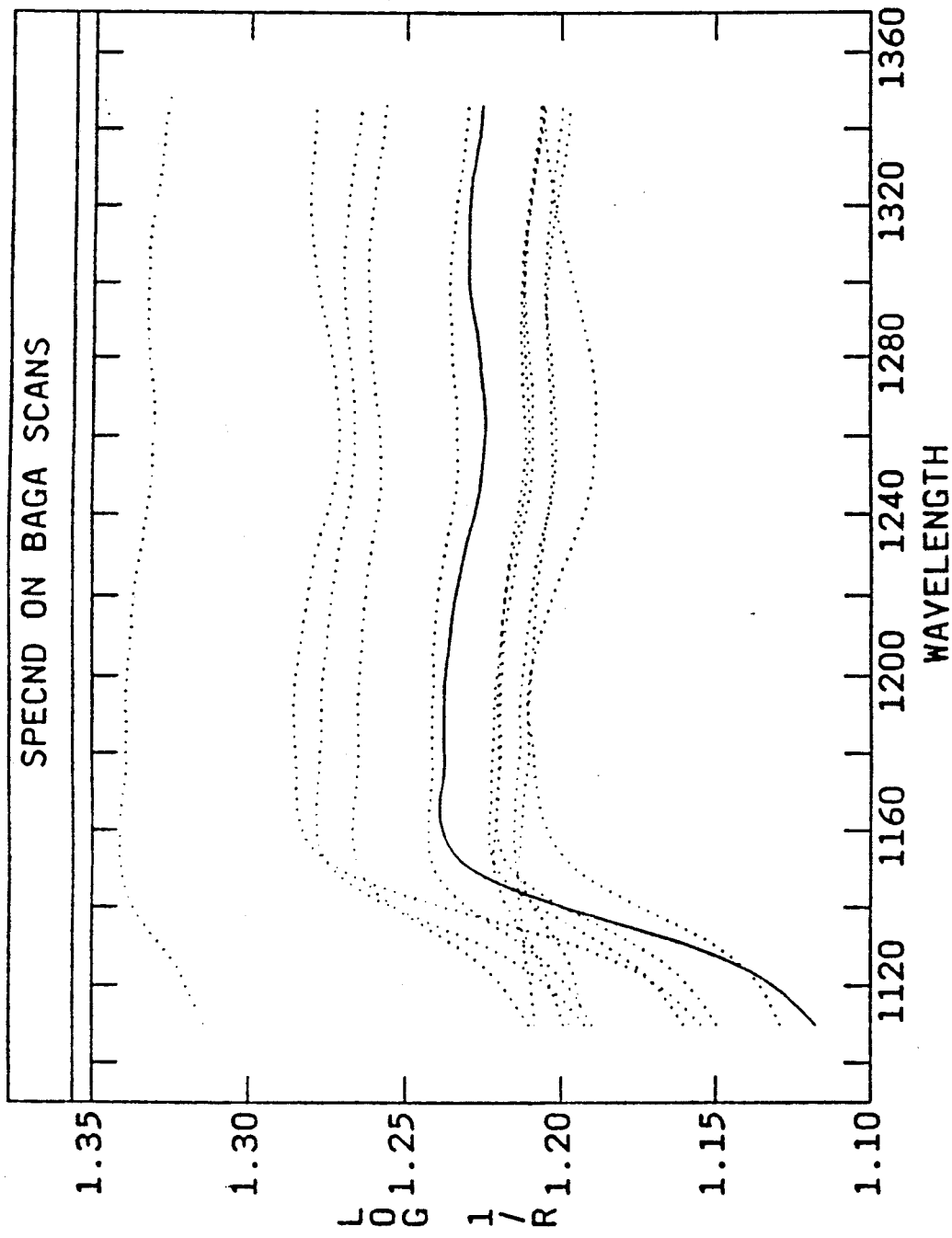
FIG. 2 is a depiction of 11 separate spectra as set forth in FIG. 1 with the exception that the IV bag of 5% dextrose solution USP and 0.5 mg per mL ranitidine has been contaminated with Pseudomonas aeruqinosa (ATCC No. 9027).
Figure 3:
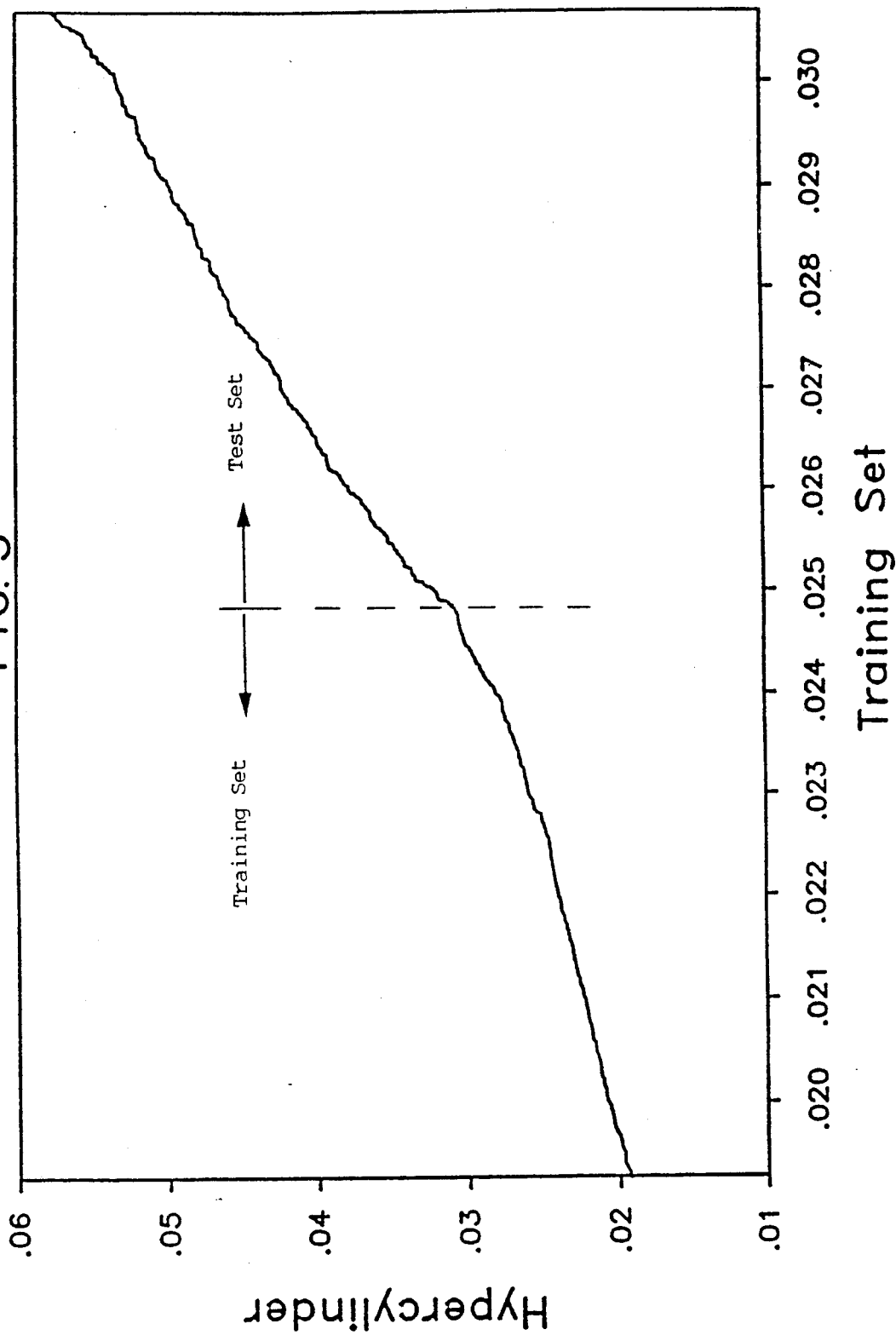
FIG. 3 is the most common appearance of a QQ plot of the training set (the points on the left half of the plot) and the test set (the points on the right half of the plot).
Figure 9:
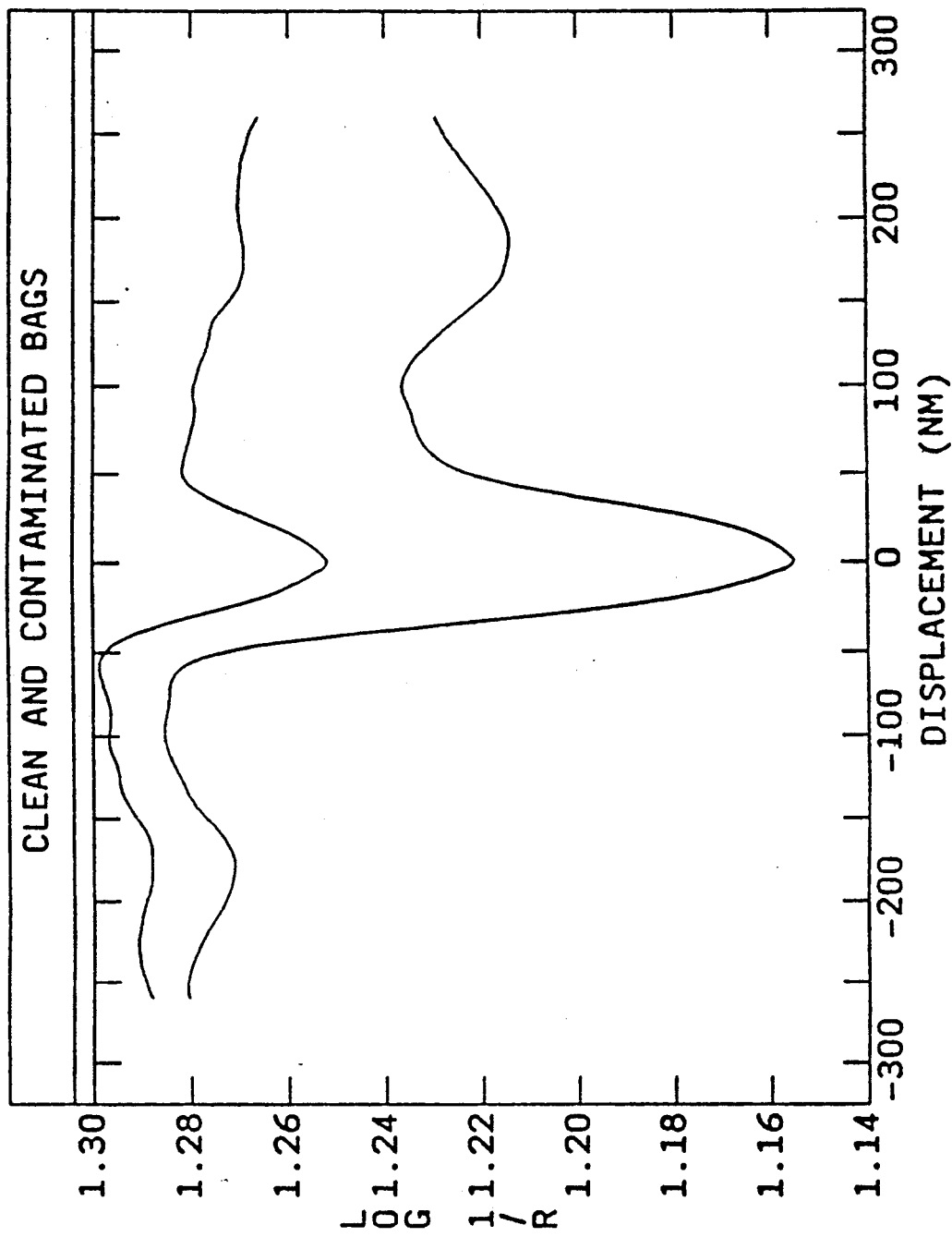
FIG. 9 depicts near-IR spectra of IV bags containing 5% dextrose and 0.5 mg/mL ranitidine after mathematical preprocessing as described herein with the upper trace being for a sterile bag and the bottom trace being for the bag contaminated with bacteria.

FIGS. 1 and 2 demonstrate why this spectra preprocessing was necessary. FIG. 1 shows 12 scans taken from an uncontaminated bag. The solid line shows the curve with the maximum absolute value of the first derivative. FIG. 2 shows 12 scans taken from a contaminated bag containing bacteria. The solid line again shows the spectrum with the maximum absolute value of the first derivative. It is evident that in clean bags, the major source of spectral variation is a baseline variation that is predominantly pathlength-dependent. In contaminated bags, however, certain spectra will show large back scattering peaks that appear as dips in the spectra near 1100 nm and 1260 nm. Other scans on the contaminated bag will show no back scattering at all. The value of the preprocessing technique for IV-bag spectra becomes apparent when one examines FIG. 9, which shows scans for both uncontaminated and contaminated IV bags. In FIG. 9, the displacement value of zero represents the back scattering observed at 1100 nm. The displacements that appear at 160 nm (both positive and negative) represent scattered light observed at 1260 nm in the original spectra. In FIG. 9, the lower curve is obtained from a contaminated bag while the upper curve is obtained from a clean uncontaminated bag. The preprocessing and filtering procedure is used to select the spectra that show the most back scattering of light, and these spectra are transformed to principal axes and used in the hyperspace integration method. Integration of spectral clusters in hyperspace begins with forming an estimate of the population distribution in hyperspace from the existing training and test sets. This estimate is formed by a bootstrap process.

The training set, test set, and validation set each have a CDF. The CDFs for the training set, test set, and validation set are given by Equations 10, 11, and 12, respectively. Plotting the elements of the vector for the training set on the abscissa versus the elements either of the test set or of the validation set on the ordinate produces a standard QQ plot. When two CDFs match, the result of the QQ plot is a straight line with a slope of 1 and an intercept of 0. However, if the two CDFs are different, bends or breaks appear in the line of the QQ plot. The presence of bends (where two lines appear in the QQ plot with different slopes) indicates the presence of two groups in hyperspace with different sizes. The presence of a break in the QQ plot line indicates two groups in space centered at different locations. The presence of both a bend and a break indicates that two groups have different sizes and locations in multidimensional hyperspace. Applying linear regression to the points on the QQ plot produces an equation whose linear coefficients have particular significance. When the spatial volume of the test set is smaller than that of the training set, the slope and intercept of the linear equation, determined by regression, have values between 0 and 1. However, when the volume of the test set is larger than that of the training set, the coefficients of the straight line through the QQ plot tend to have a large positive slope and a large negative intercept. Confidence limits are set on the correlation between the two CDFs in the QQ plot. The confidence limits are set through a bootstrap process similar to that used in equations 1-5.

Figure 10:
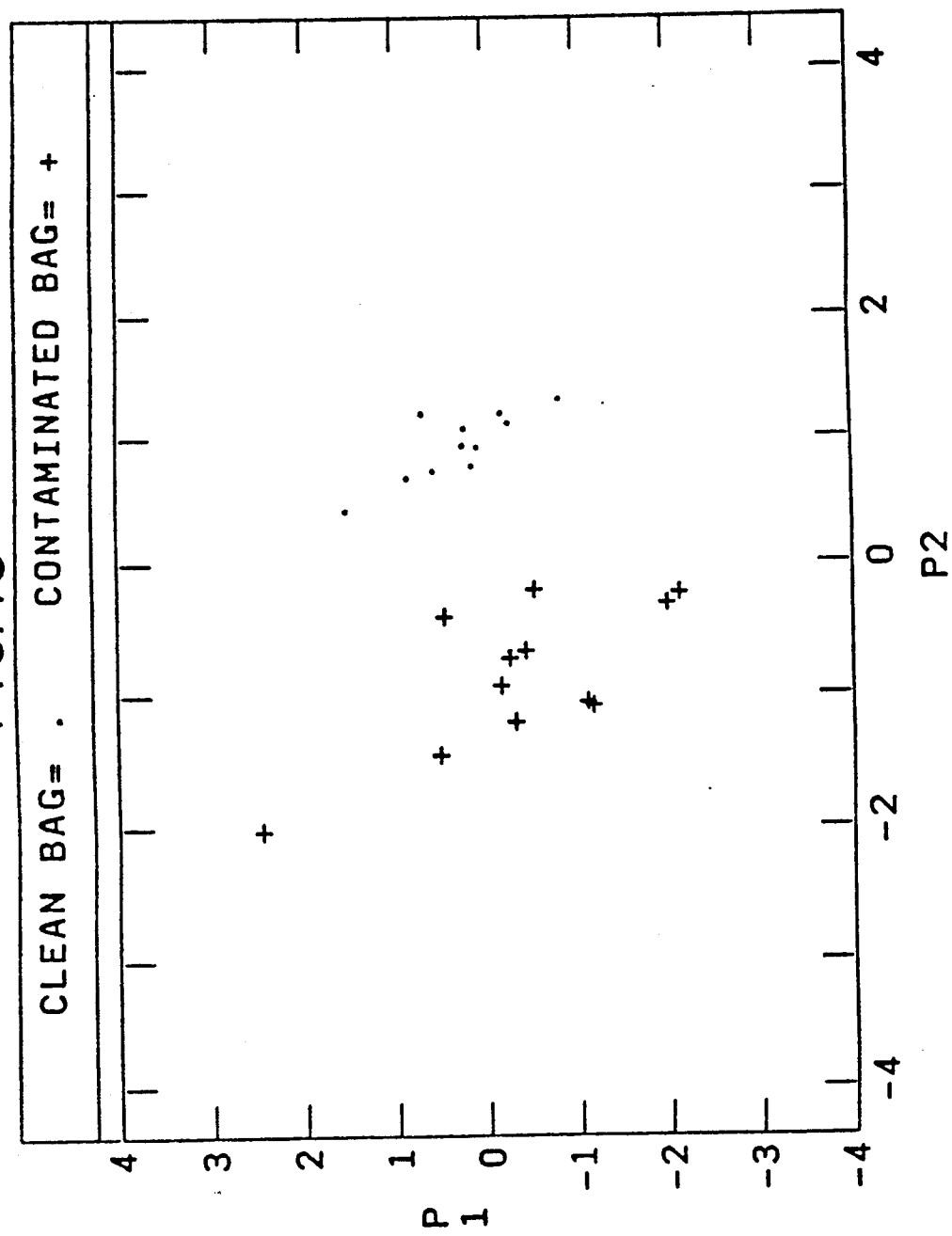
FIG. 10 depicts 12 spectra from a bag contaminated with bacteria compared to 11 spectra acquired from an uncontaminated bag.

FIG. 10 depicts the projection of spectra of a clean bag (given by points) and a contaminated bag (given by pluses) on a plane in multidimensional hyperspace. The plane corresponds to that defined by the first and second principal axes. FIG. 10 demonstrates that contaminated bags produce spectral points in hyperspace that are more widely scattered than clean bags. The larger spectral cluster of the contaminated bag occurs presumably because its spectra are more variable. The spectra in FIG. 10 represent 12 scans taken at various locations on each of the two bags (one clean bag spectrum with an A/D spike was eliminated). The fact that the pulses from the contaminated bag do not overlap the cluster formed by the points from the clean bag indicates that a spectral difference exists between the clean bag and the dirty bag. The distance between the cluster of points formed from spectra of the clean bag and the cluster formed from the contaminated bag provides an indication of the amount of material that is responsible for the contamination of the dirty bag. The direction of the displacement from the center of the clean bag provides an identifying spectrum of the material responsible for the contamination. Thus, distance gives an indication of the number of microorganisms that are present in the bag, while direction identifies the microorganisms present in the bag that are responsible for the contamination.

Figure 5:
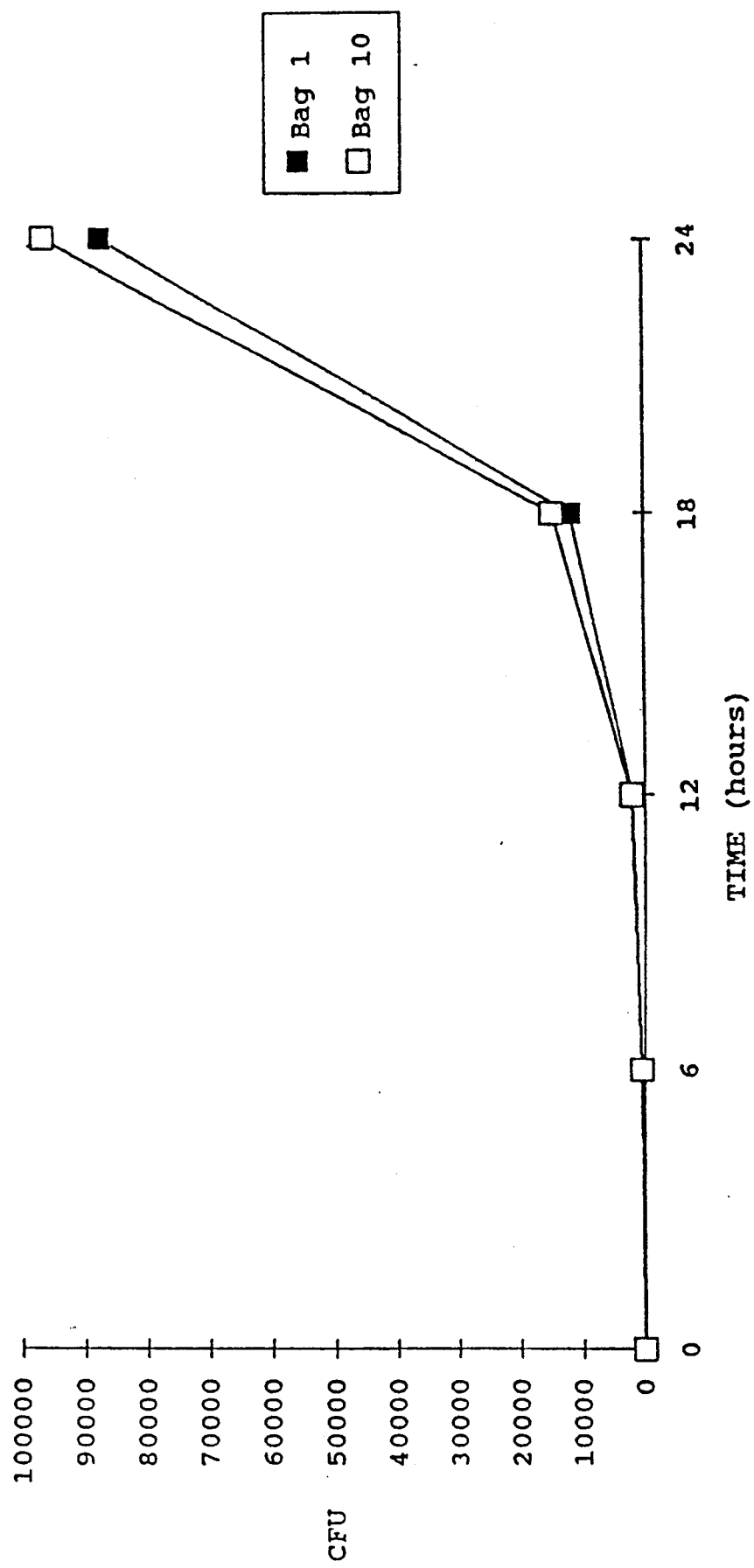
Figure 6:
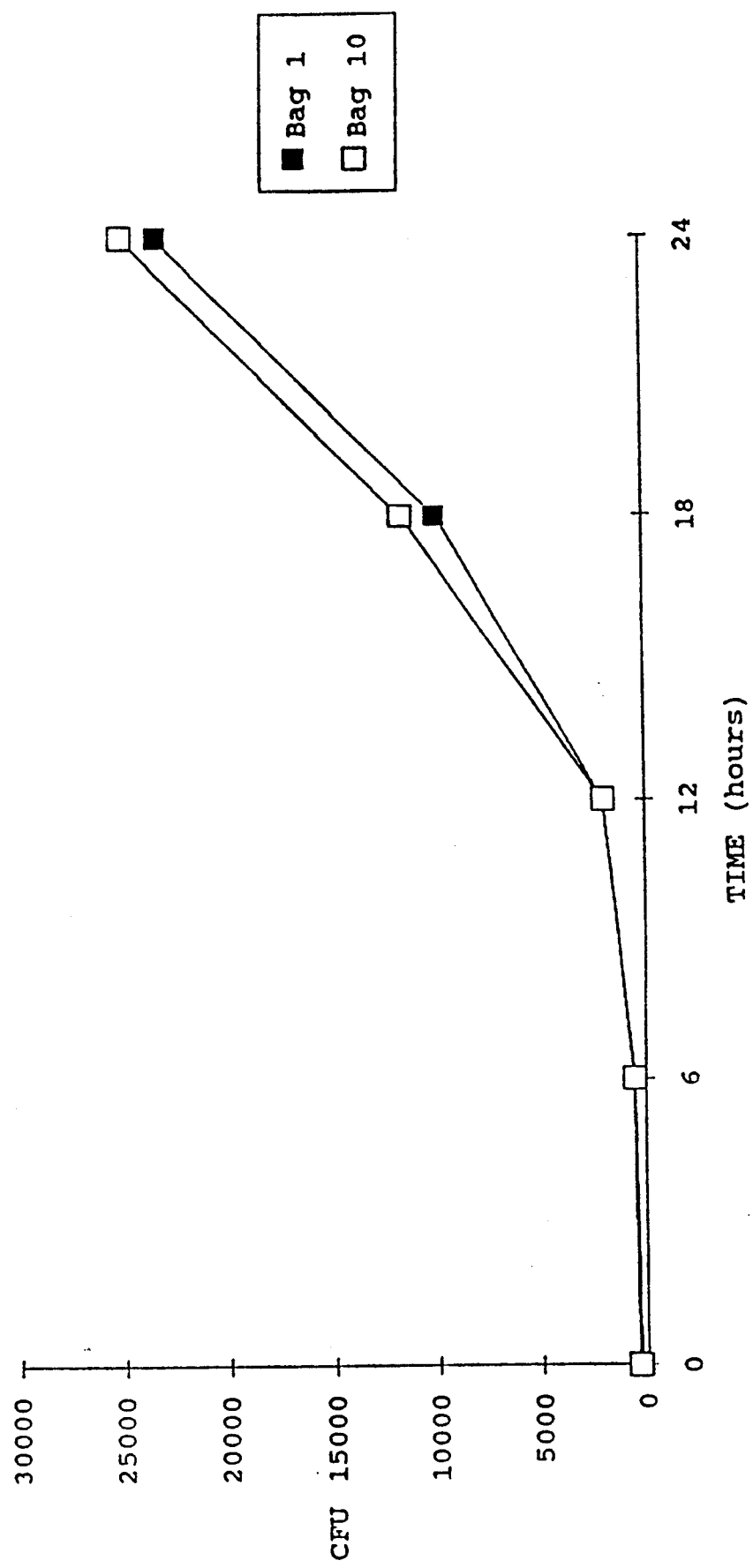

FIG. 5 gives the growth curve for the yeast, *Candida albicans*. The assay for *Candida albicans* was obtained through standard microbiological assay. The same technique was employed to determine the concentrations of the bacteria, *Pseudomonas aeruginosa*, and the mold, *Aspergillus niger*, that appear in FIGS. 4 and 6, respectively. FIG. 11 is calculated from scans that have been averaged for each of the 10 bags having the concentrations shown in FIGS. 4, 5, and 6. FIG. 11 is, in effect, a "growth curve" of sorts measured by back scattering of near-IR light from the bags and/or retroreflector. The 98% confidence limit on back scattering from clean training set is given as the horizontal short-dashed line in FIG. 11 (the level slightly above 0.93). The solid line represents the bacteria, the dotted line represents the yeast, and the dashed-dotted represents the mold. After inoculation with 165 cfu per IV bag, the bacteria (*Pseudomonas aeruginosa*) were observed at about six hrs at an average concentration of 57±4 cfu/mL per bag. After injection of 10 cfu yeast (*Candida albicans*) per bag, growth was detected at about four hrs with less than an average concentration of 3±1 cfu/mL per bag. Injection of the mold (*Aspergillus niger*) at a level of 12 cfu per bag allowed detection of growth by near-IR spectrometry at about 24 hrs at an average concentration of 145±20 cfu/mL per bag.

In FIG. 11, it appears that the yeast is the fastest growing species in the bags. However, yeast cells range in size from 3-14 μm and are larger than bacterial cells (about 0.5-2 μm). At least initially, this size advantage might make yeast a better source of light-scattering material than the bacteria, which actually grows faster. Eventually the bacterial growth appears to overtake the size advantage of yeast, and the bacteria then give the strongest back-scattering signal. Mold is intermediate in size (approximately 3-8 μm) and the slowest growing species as indicated by its continued correlation change up to nearly 50 hrs, while the correlation of the yeast and bacteria seem to have begun to level off, presumably because of the preservative (phenol) also present in the drug. What is most noticeable in FIG. 11, however, is that even at six hrs and below, the near-IR method is able to detect contamination at a 98% confidence limit for yeast and bacteria. FIGS. 4 and 5 indicate that neither the yeast nor the bacteria have grown significantly after this short period of time. Nevertheless, the near-IR method is still able to detect this contamination. The correlation between spectral clusters at six hrs is poor for *Candida albicans, Pseudomonas aeruginosa*, and *Aspergillus niger*. The poor correlation between the spectral clusters at all times (at six hrs and beyond) suggests that the near-IR method is able to differentiate between these cell types as well as possibly to provide an indication of the extent of their growth.

Summary of Results. These data suggest that changes in near-IR spectra, taken through the IV bags with a fiber optic probe and without product tampering, correlate to organism growth. Moreover, spectra also distinguish between bags contaminated with different classes of microorganisms. Integration of the method of the invention with mechanical techniques in product processing will allow an on-line sterility assurance method in parenteral-production facilities, particularly for filling processes e.g., aseptic-fill that require very careful control and monitoring because of less than desirable assurance levels. The inability in the prior art to test all parenteral units in an automated fashion is a serious limitation to conventional microbiologic testing, particularly in cases where microbial contamination is not distributed uniformly throughout a batch (Henry L. Avallone, *J. Parenter. Sci. Technol.* 1985, 39(2), 75-79 and Henry L. Avallone, *J. Parenter. Sci. Technol.* 1986, 40(2), 56-57). It is very difficult, if not impossible, to detect a small percentage of contaminated units within a large batch. Near-IR spectrometry with a fiber-optic probe according to the present invention can be used as an alternative or adjunct method to conventional microbiologic testing in quality assurance and other applications where large quantities of cells must be identified and quantified in a relatively short period of time.

The variation in replicate spectra taken from the same IV bag is larger than that observed with other containers because of the flexibility of the PVC plastic and poor near-IR transparency. To reduce the number of replicate scans needed and to improve confidence statistics, further optimization and improvements can be carried out in the sampling procedure, e.g., configuration of the optical probe, sample container and wavelength range scanned. Glass containers positioned directly in contact with the optical probe should provide even better results because glass is more rigid and offers greater transparency in the near-IR spectral region.

EXAMPLE 2

The procedure of Example 1 is repeated using glass vials in the place of PVC IV bags with, however the following changes.

Sterile and unsterile clear glass vials (10 cc, Type I borosilicate) containing a nutrient medium (Trypticase Soy Broth) were scanned for 1100-1360 nm using the identical spectrophotometer and data collection system to that described in Example 1. However, in this example, the bottom of the vials were placed directly on top the sample window of the fiber-optic diffuse-reflectance probe. Unsterile vials had been injected with one of several species of bacteria, which were allowed to grow to produce desired levels of contamination.

Ten repetitive scans of each vial were taken at slightly different positions on the bottom of the vial at 0, 6, 12, 18, 24, and 48 hrs after injection of bacteria. The spectra were filtered by a smoothing routine, and the rest of the analysis was performed as in Example 1. Test spectra recorded at these later time intervals were then compared to the "standard" spectra obtained a time zero. Such analysis allows vials that are contaminated with bacteria or other microorganisms to be distinguished from uncontaminated units.

Abbreviations:

| | |
|---|---|
| IV | intravenous |
| PVC | polyvinyl chloride |
| mL | milliliters |
| nm | nanometers |
| QQ | quantile-quantile |
| CDF | Cumulative Distribution Functions |
| near-IR | near infrared radiation |
| cfu | colony forming units |
| mg | milligrams |
| FDA | U.S. Food and Drug Administration |
| USP | United States Pharmacopeia |
| ATCC | American Type Culture Collection |
| hrs | hours |
| eq | equation |

Special defined operations:

| LIST OF SYMBOLS | |
|---|---|
| W | linear ("moving average") smoothing |
| $d(f(x))/dx$ | derivative of f(x) |
| $M(f(x),x)$ | $x \mid (d(f(x))/dx) = 0 \quad (d^2(f(x))/dx^2) < 0$ |
| r | random number on $0 < x < 1$; Monte Carlo |

-continued
LIST OF SYMBOLS

| | |
|---|---|
| | integration of continuous uniform distribution |
| K(Z) | creates a bootstrap distribution containing m elements for a set of real samples, and finds the center of this bootstrap distribution |
| [x] | the greatest-integer function of a scalar, matrix, or array |
| $\partial(x)$ | ordered elements of x (x is a matrix or array) |
| = | equals, or "is replaced by" when the same variable appears on both sides of = |

Scalars:

| | |
|---|---|
| n | the training-set, test-set, and validation-set size, i.e., the number of samples that the set contains |
| d | the number of wavelengths and the dimensionality of the analytical space |
| m | the number of sample-set replications forming a bootstrap distribution (user-determined) |
| i | an index for counting rows in a matrix or array |
| j | an index for counting columns in a matrix or array |
| $n_h$ | the number of replicate spectral points falling inside a hypercylinder |
| p | proportion of a distance distribution to trim from each end of the distribution |
| u | the number of spectra collected from a single simple bag |
| w | the number of wavelengths collected from a single sample bag |
| $s_I$ | an index marker for a wavelength region of interest |
| $p_1$ | the index number of a spectrum showing the greatest overall signal in a set of u spectra |
| $p_2$ | the index number of a spectrum showing the greatest analytical signal over a wavelength region of interest in a set of u spectra |
| $\Phi$ | the difference between the absorbances of two spectra from a single bag at the lowest wavelength |

Matrices, vectors, and arrays:

| | |
|---|---|
| $N_{(m)} = (n_{(m)j})_w$ | wavelength vector recorded by spectrometer |
| $I_{(d1)} = (i_{(d1)ij})_{u,w}$ | first derivatives of all spectra collected from a single bag |
| $I_{(1)} = (i_{(1)ij})_{u,w}$ | smoothed set of u spectra collected from a single bag |
| $I = (i_{ij})_{u,w}$ | set of u spectra as collected from a single bag |
| $I_{(d2)} = (i_{(d2)ij})_{u,w\text{-}s_I}$ | first derivative of region of interest |
| $I_{(s1)} = (i_{(s1)i})_u$ | sum of absolute value of first derivative of full spectra |
| $I_{(s2)} = (i_{(s2)i})_u$ | sum of absolute value of first derivative of wavelength region of spectral interest |
| $H_{(1)} = (h_j)_w$ | spectrum selected by the index $p_1$ |
| $H_{(2)} = (h_j)$ | spectrum selected by the index $p_2$ |
| $B = (b_{ij})_{m,d}$ | m-by-d bootstrap distribution of training-set sample spectra |
| $B_{(X)} = (b_{ij})_{m,d}$ | bootstrap distribution of test-setsample spectra |
| $B_{(V)} = (b_{ij})_{m,d}$ | bootstrap distribution of validation-set sample spectra |
| $C = (c_j)_d$ | center of the bootstrap distribution B |
| $P = (p_{ij})_{m,n}$ | training-set sample numbers selected for the bootstrap-sample sets used to calculate bootstrap distribution |
| $T = (t_{ij})_{n,d}$ | training-set sample spectra |
| $X = (x_{ij})_{n,d}$ | test-set sample spectra |
| $V = (v_{ij})_{n,d}$ | validation-set sample spectra |
| $K = (k_j)_n$ | training-set sample numbers selected for a particular bootstrap sample |
| $B_{(s)} = (b_{(s)ij})_{n,d}$ | bootstrap sample set used to calculate single rows of a bootstrap distribution (B, $B_{(X)}$, or $B_{(V)}$) |
| $S_{(T)} = (s_{(T)i})_m$ | Euclidean distances of training-set replicates from C, the center of the bootstrap distribution of the training set |
| $S_{(X)} = (s_{(X)i})_m$ | Euclidean distances of test-set replicates from C |
| $S_{(V)} = (s_{(V)i})_m$ | Euclidean distances of validation-set replicates from C |
| $P_{(T)} = (p_i)_{m\text{-}2pm}$ | set of (m-2pm) indices used for trimming distance distributions |
| $C_{(t)} = (c_{(t)i})_{2m\text{-}4pm}$ | cumulative distribution function (CDF) formed by the trimmed and ordered elements of the training-set bootstrap distribution; CDF has (2m-4pm) elements |
| $C_{(X)} = (c_{(X)i})_{2m\text{-}4pm}$ | CDF formed by the trimmed and ordered elements of the test-set and training-set bootstrap distributions |
| $C_{(V)} = (c_{(V)i})_{2m\text{-}4pm}$ | CDF formed by the trimmed and ordered elements of the validation-set and training-set bootstrap distributions |

What is claimed is:

1. A method of detection of microorganisms in a liquid sample to be tested, which comprises i) obtaining near infrared spectra in the range of about 1100 to 1360 nanometers of said liquid sample at a plurality of locations within said liquid sample, ii) obtaining a near infrared spectrum in the range of about 1100 to 1360 nanometers of a standard sample and iii) comparing said liquid sample spectra to said standard sample spectrum with computer assistance.

2. The method of claim 1, wherein said liquid sample is an aqueous liquid sample.

3. The method of claim 1, wherein said microorganisms are yeast bacteria or mold.

4. The method of claim 1, wherein said liquid sample is held in a container, which is at least partially transparent to at least one wavelength of near-infrared light.

5. The method of claim 4, wherein said container is a container of glass or a polymer.

6. The method of claim 5, wherein said polymer is polyvinyl chloride.

7. The method of claim 1, wherein said liquid sample comprises water and dextrose or sodium chloride.

8. The method of claim 1, wherein said liquid sample comprises a 5% (w/v) aqueous dextrose solution or a 0.9% (w/v) aqueous sodium chloride solution.

9. The method of claim 1, wherein said comparison of the near-infrared spectrum of said liquid sample to that of the standard sample is a comparison of the near-infrared scattering spectra of said liquid sample and said standard sample.

10. The method of claim 1, wherein said method is a method for determining the sterility of an aseptically-filled container for parenteral administration of its liquid contents to a human.

11. The method of claim 10, wherein said parenteral administration is intravenous administration.

12. The method of claim 1, wherein said standard sample has a known quantity of said microorganisms.

13. The method of claim 1, wherein said comparison is carried out by comparing the spectral distribution quantiles of the liquid sample to be tested with the standard as to scale location and shape.

14. The method of claim 1 wherein said near infrared spectra are obtained at 10 or more locations within said liquid sample.

* * * * *